US006486374B1

United States Patent
Radcliffe et al.

(10) Patent No.: US 6,486,374 B1
(45) Date of Patent: Nov. 26, 2002

(54) METHOD AND APPARATUS FOR ALKYLATION USING SOLID CATALYST PARTICLES IN A TRANSPORT REACTOR

(75) Inventors: William H. Radcliffe, Prospect Heights, IL (US); Wesley L. Kiel, Des Plaines, IL (US); Christopher D. Gosling, Roselle, IL (US); Paul A. Sechrist, Des Plaines, IL (US); Paul Anderson, Palatine, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/249,749

(22) Filed: Feb. 12, 1999

Related U.S. Application Data

(60) Provisional application No. 60/076,021, filed on Feb. 26, 1998.

(51) Int. Cl.⁷ .......................... C07C 15/067; C07C 2/56
(52) U.S. Cl. ...................... 585/714; 585/446; 585/451; 585/716; 585/719; 585/721; 585/921; 585/924; 585/926
(58) Field of Search ................................. 585/446, 447, 585/450, 451, 714, 716, 719, 721, 921, 922, 923, 924, 926; 422/144, 145, 147

(56) References Cited

U.S. PATENT DOCUMENTS

| | | | | |
|---|---|---|---|---|
| 3,662,020 A | * | 5/1972 | Hemminger et al. ... | 260/683.43 |
| 5,198,595 A | * | 5/1972 | Lee et al. .................... | 585/467 |
| 4,094,923 A | * | 6/1978 | Dixon .................... | 260/683.48 |
| 4,202,673 A | | 5/1980 | Knowlton .................. | 48/86 R |
| 5,012,033 A | * | 4/1991 | Child et al. ................. | 585/722 |
| 5,489,732 A | | 2/1996 | Zhang et al. ............... | 585/467 |
| 5,672,797 A | | 9/1997 | Kocal .......................... | 585/467 |

OTHER PUBLICATIONS

Grbavcic, Z.B. et al. Fluid Flow Pattern and Solids Circulation Rate in a Liquid Phase Spout–Fluid Bed with Draft Tube. The Canadian Journal of Chemical Engineering, vol. 70, (Oct. 1992) pp. 895–904.
Gas Fluidization Technology edited by D. Geldart, (John Wiley and Sons, Great Britain 1986) pp. 362–407 TP156.F65G37.
Knowlton, T.M. and Hirsan, I. L–Valves Characterized for Solids Flow. Hydrocarbon Processing, (Mar. 1978) pp. 149–156.
Liang, W.–G. et al. Radial Nonuniformity of Flow Structure in a Liquid–Solid Circulating Fluidized Bed. Chemical Engineering Science, vol. 51, No. 10., pp. 2001–2010, (Great Britain 1996).

* cited by examiner

Primary Examiner—Thuan D. Dang
(74) Attorney, Agent, or Firm—John G. Tolomei; James C. Paschall; Michael A. Moore

(57) ABSTRACT

A method and apparatus for alkylating an alkylation substrate with an alkylating agent in the presence of solid catalyst particles in a transport reactor is disclosed. Solid catalyst particles in the transport reactor effluent recirculate to the inlet of the transport reactor through one or more conduits. The rate through each conduit is regulated by fluid-controlled valves that use the alkylation substrate as the regulating fluid. This method and apparatus help ensure uniform or symmetric flow of catalyst from the effluent of the transport reactor to the bottom of the transport reactor. This method and apparatus also help ensure uniform or symmetric flow of alkylation substrate to the bottom of the transport reactor with minimal bypassing by the alkylating agent around of the transport reactor. This invention finds use in the production of motor fuels by the alkylation of liquid hydrocarbons in the presence of solid catalyst particles.

16 Claims, 3 Drawing Sheets

METHOD AND APPARATUS FOR ALKYLATION USING SOLID CATALYST PARTICLES IN A TRANSPORT REACTOR

CROSS-REFERENCE TO RELATED APPLICATION

This application claims the benefit of U.S. Provisional Application No. 60/076,021, filed on Feb. 26, 1998.

FIELD OF THE INVENTION

This invention relates to the alkylation of hydrocarbons such as aromatics and paraffins to produce useful chemicals and motor fuel. This invention specifically relates to a method and apparatus for alkylation using a transport reactor.

BACKGROUND OF THE INVENTION

Hydrocarbon alkylation is widely used in the petroleum refining and petrochemical industries to produce a variety of useful acyclic and cyclic hydrocarbon products which are consumed in motor fuel, plastics, detergent precursors, and petrochemical feedstocks. Alkylation processes generally involve the alkylation of an alkylation substrate with an alkylating agent. The alkylation substrate is an aromatic hydrocarbon such as benzene if the process produces ethylbenzene, cumene, or linear alkyl benzenes. If the process produces motor fuels such as gasoline, the alkylation substrate may be a branched paraffinic hydrocarbon having from 4 to 6 carbon atoms. The alkylating agent is typically an olefinic hydrocarbon containing from 2 to about 20 carbon atoms, depending on the desired product of the process.

Much of the installed base of alkylation capacity uses liquid phase hydrofluoric acid, generally referred to as HF, as the catalyst. The use of HF in these applications has a long record of highly dependable and safe operation. However, the potential damage from an unintentional release of any sizable quantity of HF and the need to safely dispose of some byproducts produced in the process has led to an increasing demand for alkylation process technology which does not employ liquid phase HF as the catalyst.

Numerous solid alkylation catalysts have been described in the open literature. However, these catalysts appear to suffer from unacceptably high deactivation rates when employed at commercially feasible conditions. While some catalysts have a sufficiently useful lifetime to allow the performance of alkylation, the rapid change in activity results in a change in product composition and also requires the periodic regeneration of the catalyst with the accompanying removal of the reaction zone from operation. It is very desirable to provide a continuous process for alkylation which is not subjected to periodic reaction zone stoppages or variation in the product stream composition.

Transport reactors are commonly used in hydrocarbon processing. In a transport reactor, the catalyst bed as a whole moves. Thus, a transport reactor can be contrasted with a fixed bed catalytic reactor and with an ebullated bed catalytic reactor. In a fixed bed reactor the catalyst particles do not move, and in an ebullated bed reactor the catalyst particles are suspended in a fluid but the settling velocity of the catalyst particles balances the fluid upflow velocity so that the catalyst bed as a whole does not move. Although it is generally the case that the direction of catalyst flow through a transport reactor is upward, the direction may also be downward, horizontal, a direction that is intermediate between vertical and horizontal, or a combination of these directions.

When the direction of catalyst flow through a transport reactor is upward, the transport reactor is often called a riser-reactor. Riser-reactors are commonly used in hydrocarbon processing, such as fluidized catalytic cracking and more recently in fluidized solid bed motor fuel alkylation. In a common arrangement, a fluid hydrocarbon reactant engages a solid hydrocarbon conversion catalyst at the bottom of a riser-reactor and transports the catalyst in a fluidized state up the riser-reactor. During the ascent through the riser-reactor, the catalyst promotes certain desired conversion reactions among the reactants in order to produce desired products. A stream of catalyst and hydrocarbon products, by-products, and unreacted reactants if any discharges from the top of the riser-reactor into a separation zone. The hydrocarbons and the catalyst disengage in the separation zone, with the hydrocarbons being withdrawn overhead for recovery and the catalyst dropping by gravity to the bottom of the separation zone. Despite some deactivation that may have occurred to the catalyst in the riser-reactor, some of the catalyst that collects at the bottom of the separation zone usually has enough residual activity that it can be reused in the riser-reactor without first being withdrawn from the separation zone for regeneration. Such still active catalyst is recirculated through a recirculation conduit from the bottom of the separation zone to the bottom of the riser-reactor, where the catalyst contacts reactants again.

Several methods are used for controlling the introduction of reactants and for controlling the recirculation of catalyst to the bottom of the riser-reactor. For example, one method is shown in a motor fuel alkylation process in U.S. Pat. No. 5,489,732 (Zhang et al.). Isoparaffins and olefins are introduced into the bottom of the riser-reactor, and the flow of catalyst through a single recirculation conduit to the bottom of the riser-reactor is controlled by several means including slide valves, other types of valves, lock hoppers, fluid flow control (reverse flow of liquid), screw conveyors, and L-valves. This patent also teaches that one reactant, isobutane, can also be introduced into the recirculation conduit for the purpose of flushing by-product hydrogen from the recirculating catalyst. This method, however, is not suitable for withdrawing catalyst symmetrically or uniformly from the bottom of the separation zone, if the bed of catalyst in the bottom of the separation zone is not totally fluidized in the axial direction, i.e., it is a moving packed bed or a bed that is merely at incipient fluidization. In these types of beds, catalyst that is below the angle of repose from the opening to the recirculation pipe remains stagnant, which leads to inefficient use of the separation zone. Areas of stagnant catalyst can lead to operational difficulties if, because of an upset or disruption, the stagnant catalyst breaks loose, enters the recirculation pipe, and enters the riser-reactor. Another method that uses a spout-fluid bed with a draft tube is shown in the article by H. Littman et al. entitled "Fluid Flow Pattern and Solids Circulation Rate in a Liquid Phase Spout-Fluid Bed with Draft Tube," *The Canadian Journal of Chemical Engineering*, Vol. 70, October 1992, pp. 895–904. This method provides poor control of the fraction of the total flow rate of reactants to the bottom of the draft tube that would flow through the draft tube compared to that fraction which would flow in reverse flow through the annular bed around the draft tube and would effectively bypass the draft tube. Moreover, this method provides poor control of the catalyst flow rate to the bottom of the draft tube, once the geometry around the bottom of the draft tube is fixed.

Accordingly, there is a need for a method and an apparatus that is suitable for use in a transport reactor process that uniformly or symmetrically withdraws catalyst from the separation zone which separates the transport reactor effluent, that uniformly or symmetrically controls the flow of reactants to the bottom of the transport reactor, and that controls the flow of catalyst from the separation zone to the transport reactor.

SUMMARY OF THE INVENTION

This invention is a novel method and apparatus for alkylating an alkylation substrate with an alkylating agent using solid catalyst particles in a fluidized transport reactor. The effluent of the transport reactor passes to a separation zone, which separates the product alkylate from the solid catalyst particles. The solid catalyst particles recirculate from the separation zone to the transport reactor through two or more recirculation conduits. The recirculation rate of catalyst particles through each recirculation conduit is regulated by a fluid-controlled valve that uses the alkylation substrate as the regulating fluid. Each fluid-controlled valve discharges catalyst through a conduit into the transport reactor, so that a single, common transport reactor is fed by all of the fluid-controlled valves. This invention is particularly applicable to transport reactors that are riser-reactors.

This method and apparatus have numerous advantages over the prior art. By using two or more recirculation conduits rather than a single conduit, this invention can help to ensure uniform residence time distribution of catalyst particles and to minimize areas of stagnant catalyst particles in the separation zone. This, in turn, helps prevent unexpected changes in riser-reactor performance that can occur when catalyst particles of varying activity enter the riser-reactor. This invention also helps ensure that the upward flow of reactants is through the riser-reactor rather than through the recirculation pipes, which helps prevent bypassing of the riser-reactor by the reactants. In addition, by having all fluid-controlled valves feed into a single, common riser-reactor rather than to a separate riser-reactor for each fluid-controlled valve, this invention is simpler to build and operate.

It is an objective of this invention to provide an alkylation process which does not employ liquid phase HF as the catalyst. It is a further objective of the subject invention to provide an alkylation process which utilizes a solid catalyst. It is a specific objective of the invention to provide a solid catalyst alkylation process for the alkylation of liquid hydrocarbons for the production of motor fuel blending hydrocarbons.

Accordingly, in one embodiment, this invention is a process for the alkylation of an alkylation substrate with an alkylating agent. An alkylating agent, a feed stream comprising an alkylation substrate, a first recirculation stream, and a second recirculation stream pass to an alkylation transport reactor. The first recirculation stream and the second recirculation stream each comprise catalyst particles and the alkylation substrate. In the alkylation transport reactor, the alkylating agent alkylates the alkylation substrate in the presence of a fluidized bed of catalyst particles at alkylation conditions, thereby producing alkylate. A transport reactor effluent stream comprising alkylate and catalyst particles passes from the alkylation transport reactor to a separation zone, where the transport reactor effluent stream is separated. Catalyst particles and a product stream comprising alkylate are recovered from the separation zone. A first portion of the catalyst particles recovered from the separation zone pass to a first fluid-controlled valve. The flow of alkylation substrate into the first fluid-controlled valve is regulated to produce the first recirculation stream and to deliver catalyst particles to the alkylation transport reactor. A second portion of the catalyst particles recovered from the separation zone pass to a second fluid-controlled valve, and the flow of alkylation substrate into the second fluid-controlled valve is regulated to produce the second recirculation stream and to deliver catalyst particles to the alkylation transport reactor.

In a more detailed embodiment, this invention is a process for the alkylation of isobutane with butenes. A feed stream comprising isobutane, a first recirculation stream comprising catalyst particles and isobutane, and a second recirculation stream comprising catalyst particles and isobutane passing into a substantially vertical alkylation riser-reactor. The riser-reactor has a bottom portion and a top portion that is oriented above the bottom portion, and the feed stream, the first recirculation stream, and the second recirculation stream enter the bottom portion of the riser-reactor. Butenes pass to the bottom portion of the riser-reactor and to at least three intermediate portions of the riser-reactor, where the at least three intermediate portions are located between the bottom portion and the top portion of the riser-reactor. The butenes alkylate isobutane in the presence of a fluidized bed of catalyst particles at alkylation conditions in the riser-reactor, and produce alkylate. A riser-reactor effluent stream discharges from the top portion of the riser-reactor to a separation zone. The riser-reactor effluent stream comprises alkylate and catalyst particles that are partially deactivated. In the separation zone, the riser-reactor effluent stream is separated into a product stream comprising alkylate and into catalyst particles that are partially deactivated. The product stream is recovered from the process, and the catalyst particles pass downwardly in the separation zone. In a lower portion of the separation zone, a dense fluidized bed forms. The dense fluidized bed contains catalyst particles that are partially deactivated. In the dense fluidized bed, isobutane and hydrogen contact the catalyst particles at reactivation conditions sufficient to at least partially reactivate the catalyst particles. After being contacted with isobutane and hydrogen, a first aliquot portion of catalyst particles passes from the separation zone to a substantially vertical first recirculation conduit. In the first recirculation conduit, the catalyst particles form a first moving packed bed. The catalyst particles pass downwardly through the first moving packed bed to a first fluid-controlled valve. The flow of isobutane into the first fluid-controlled valve is regulated to produce the first recirculation stream and to deliver catalyst particles to a horizontal first feeder conduit. The first recirculation stream is conveyed through the first feeder conduit and to the bottom portion of the riser-reactor. A second aliquot portion of catalyst particles, after being contacted with isobutane and hydrogen, passes from the separation zone to a substantially vertical second recirculation conduit, where the catalyst particles form a second moving packed bed. The catalyst particles pass downwardly through the second moving packed bed to a second fluid-controlled valve. The flow of isobutane into the second fluid-controlled valve is regulated to produce the second recirculation stream and to deliver catalyst particles to a horizontal second feeder conduit. The second recirculation stream is conveyed through the second feeder conduit and to the bottom portion of the riser-reactor.

In another embodiment, this invention is an apparatus for alkylating liquid hydrocarbons using solid catalyst particles. A substantially vertical transport reactor has a reactor inlet and a reactor outlet. The reactor inlet and the reactor outlet in part define a reactor space for maintaining a bed of solid catalyst particles and liquid hydrocarbons. A means for discharging solid catalyst particles and liquid hydrocarbons from the transport reactor communicates with the reactor outlet of the transport reactor. A means for disengaging solid catalyst particles and liquid hydrocarbons communicates with the means for discharging. A vessel is in communication with the means for disengaging. The vessel has a means for receiving solid catalyst particles from the means for disengaging. In addition, the vessel has a vessel outlet that in part defines a vessel space for maintaining a bed of solid catalyst particles. A first recirculation conduit, which extends in a substantially vertical direction, has first conduit inlet that is in communication with the vessel outlet for receiving solid catalyst particles. The first recirculation conduit also has a first conduit outlet. A first valve conduit has a first valve inlet in communication with the first conduit outlet for receiving solid catalyst particles and a first valve outlet in communication with the reactor inlet for discharging solid catalyst particles. The first valve conduit also has a first means for introducing liquid hydrocarbons at a controlled rate into the first valve conduit between the first valve inlet and the first valve outlet. A second recirculation conduit, which extends in a substantially vertical direction, has a second conduit inlet that is in communication with the vessel outlet for receiving solid catalyst particles. The second recirculation conduit also has a second conduit outlet. A second valve conduit has a second valve inlet in communication with the second conduit outlet for receiving solid catalyst particles and a second valve outlet in communication with the reactor inlet for discharging solid catalyst particles. The second valve conduit also has a second means for introducing liquid hydrocarbons at a controlled rate into the second valve conduit between the second valve inlet and the second valve outlet. Means are provided for introducing liquid hydrocarbons into the reactor inlet.

INFORMATION DISCLOSURE

Figure 1:
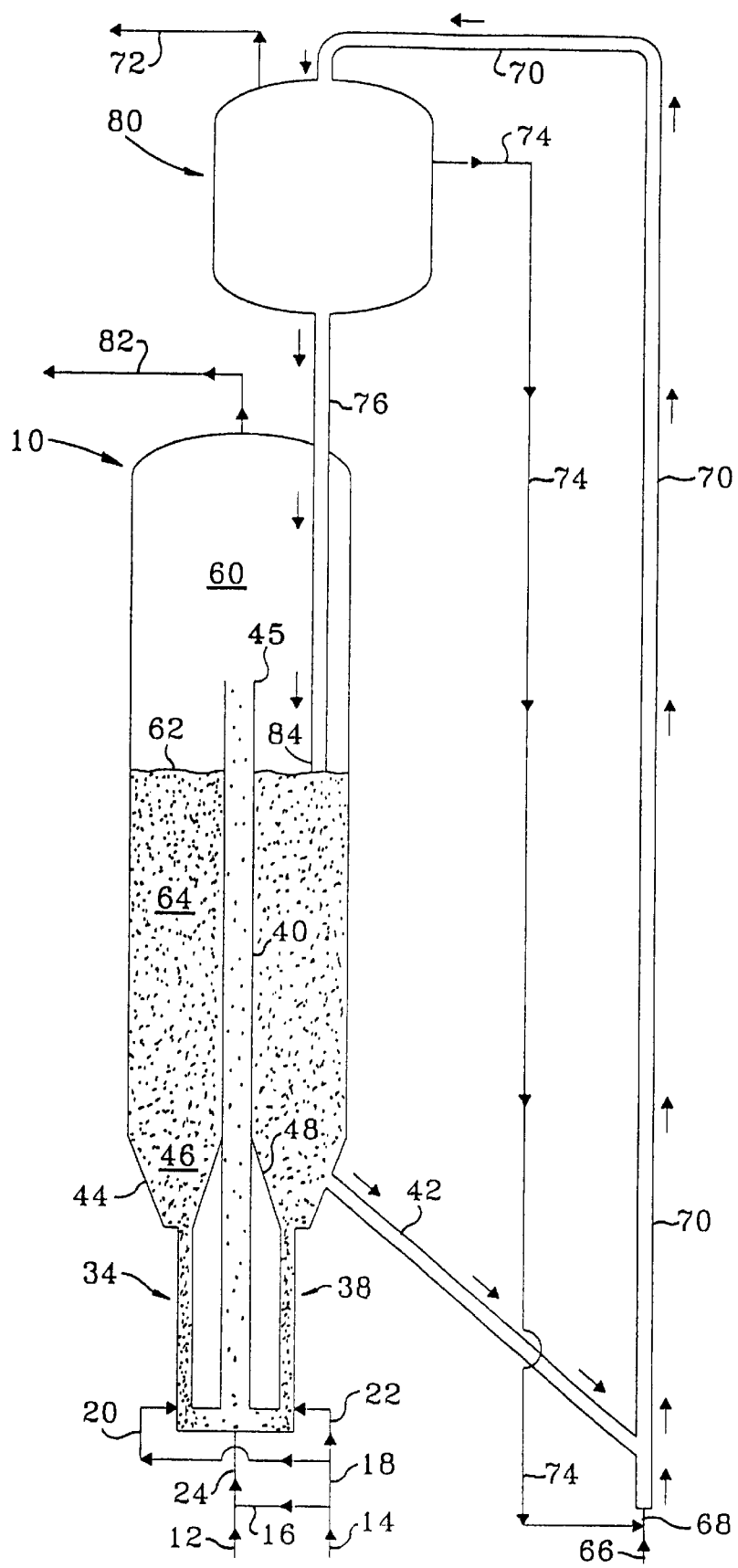
FIG. 1 shows a flow diagram of an alkylation process that uses an embodiment of this invention.

U.S. Pat. No. 5,489,732 (Zhang et al.) teaches a solid bed motor fuel alkylation process where isobutane is introduced into the bottom of a riser-reactor and into a catalyst recirculation conduit that flows into the bottom of the riser-reactor and where the flow of catalyst through the recirculation conduit can be by fluid flow control (reverse flow of liquid.) The teachings of U.S. Pat. No. 5,489,732 are incorporated herein by reference.

Theory and experimental data on the operation of spouted beds and spout-fluid beds, with and without draft tubes, are described in H. Littman et al., "Fluid Flow Pattern and Solids Circulation Rate in a Liquid Phase Spout-Fluid Bed with Draft Tube," *The Canadian Journal of Chemical Engineering*, Vol. 70, October 1992, pp. 895–904.

Fluid-controlled valves, which are also called nonmechanical-valves, include L-valves, J valves, and K valves, which are described in an article titled "L-valves Characterized for Solid Flow" beginning at page 149 in the March, 1978 issue of *Hydrocarbon Processing*, in the text entitled *Gas Fluidization Technology*, edited by D. Geldart and published by John Wiley and Sons in 1986, and in U.S. Pat. No. 4,202,673.

A liquid-solid circulating fluidized bed apparatus that uses a distribution section consisting of a pipe distributor and a porous plate distributor is described in the article by W. G. Liang et al., entitled "Radial Nonuniformity of Flow Structure in a Liquid-Solid Circulating Fluidized Bed," *Chemical Engineering Science*, Vol. 51, No. 10, pp. 2001–2010, 1996.

DETAILED DESCRIPTION OF THE INVENTION

The alkylation substrate for this invention may be essentially any hydrocarbon which is retained as an easily flowable liquid phase material and which may be alkylated via solid catalyst at the conditions employed in the transport reactor. The alkylation substrate may be an aromatic hydrocarbon, if the objective is to produce such chemicals as ethylbenzene and cumene or to produce linear alkyl benzenes which are sulfonated to detergents. Although benzene is the principal aromatic of interest, aromatics such as alkyl-substituted benzenes, condensed ring systems generally, and alkylated derivatives thereof may be used. Examples of such aromatics are toluene, ethylbenzene, propylbenzene, and so forth; xylene, mesitylene, methylethylbenzene, and so on; naphthalene, anthracene, phenanthrene, methylnaphthalene, dimethylnaphthalene, and tetralin. More than one aromatic can be used. If, on the other hand, the objective is to produce motor fuels, then the alkylation substrate may be a paraffinic hydrocarbon, such as branched paraffins having from 4 to 6 carbon atoms. Suitable paraffinic hydrocarbons are illustrated by 2-methylpropane (commonly called isobutane), 2-methylbutane (or isopentane), 2,3-dimethylbutane, 2-methylpentane, and 3-methylpentane.

The alkylation substrate is alkylated with an alkylating agent. If the objective is to produce chemicals such as ethylbenzene or cumene or to produce motor fuels, then the alkylating agent is typically an olefinic hydrocarbon containing from 2 to about 6 carbon atoms. Examples of such olefins include ethylene, propylene, 1-butene, cis-2-butene, trans-2-butene, and iso-butene. However, if the objective is to produce linear alkyl benzenes, then the alkylating agent can be an olefinic hydrocarbon having from about 2 to about 20 carbon atoms, and usually from about 10 to about 15 carbon atoms. More than one olefin may be used. The alkylating agent may be chosen also from a variety of compounds other than olefins including monohydric alcohols. Suitable alcohols include ethanol and methanol. For instance, methanol is widely described in the literature as being useful in the methylation of benzene and toluene.

FIGS. 1–5 show embodiments of the process and apparatus of the subject invention. For clarity and simplicity, some items associated with the operation of the embodiments have not been shown. These items include flow and pressure control valves, pumps, heat exchangers, temperature and pressure monitoring systems, vessel internals, etc., which may be of customary design. FIGS. 1–5 are not intended to limit the scope of the present invention as set forth in the claims. In addition, the description that follows is written in terms of isobutane as the alkylation substrate and a mixture of butene isomers as the alkylation agent, but the following description is also not intended to limit the scope of the invention as set forth in the claims. The product, which comprises hydrocarbons having from 5 to 12 or more carbon atoms, may be recovered by conventional product recovery methods such as fractional distillation, which need not be described herein. A particularly preferred product is $C_8$ hydrocarbons.

Figure 2:
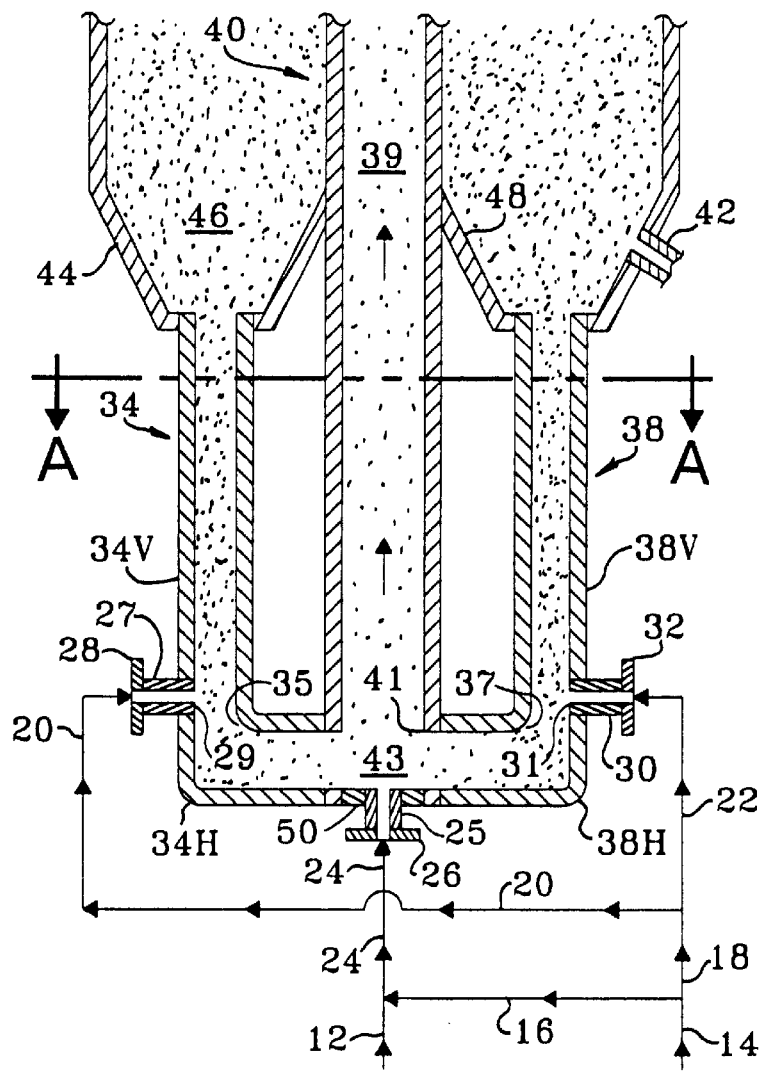
FIG. 2 shows details of part of FIG. 1.
Figure 3:
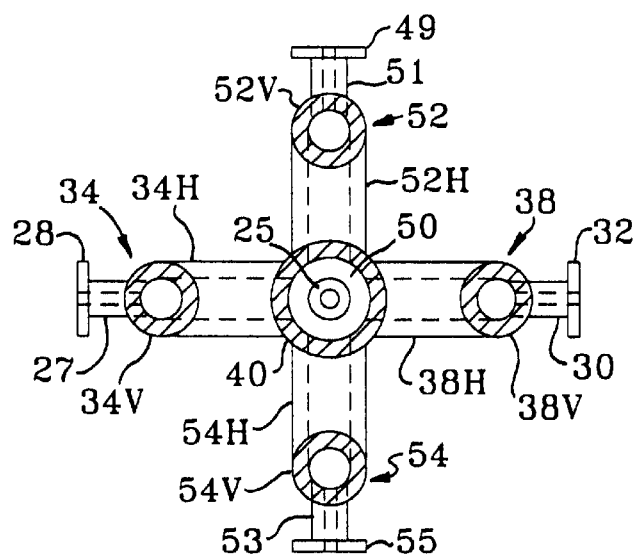
FIG. 3 shows Section A—A of FIG. 2.

Referring now to FIGS. 1, 2, and 3, a liquid phase stream comprising isobutane enters the process through a line 14, and a liquid phase stream comprising butene isomers enters through a line 12. A portion of the isobutane in the line 14 passes through a line 16, combines with the stream in the line 12, and the combined stream flows through a line 24. The flow rates of the streams flowing through lines 12 and 16 are regulated by valves (not shown). The combined stream enters vessel 10 through a flang 26 and a nozzle 25 at a point below the bottom 41 of a substantially vertical riser-reactor 40. The term "substantially vertical" as used herein means preferably less than 3°, more preferably less than 0.5°, and most preferably less than 0.2°, from the vertical. The nozzle 25 extends from the flange 26 through a circular bottom cover 50 of the riser-reactor 40, with the upper end of nozzle 25 being preferably flush with the inside surface of the bottom cover 50. The remaining portion of the stream in the line 14 flows through a line 18 and is divided into four portions that each flow through a line to one of four fluid-controlled L-valves that are generally denoted 34, 38, 52, and 54. Each L-valve has a port comprising a flange and a nozzle for introducing that portion of the stream in the line 18 that flows to that L-valve. Isobutane is introduced to the L-valve 34 by a flange 28 and a nozzle 27, to the L-valve 38 by a flange 32 and a nozzle 30, to the L-valve 52 by a flange 49 and a nozzle 51, and to the L-valve 54 by a flange 55 and a nozzle 53. One portion of the stream in the line 18 flows through a line 20 and enters L-valve 34 via the flange 28 and the nozzle 27, and another portion flows through a line 22 and enters L-valve 38 via the flange 32 and the nozzle 30. The third and fourth portions flow through lines (not shown), with the third portion entering L-valve 52 via the flange 49 and the nozzle 51 and the fourth portion entering L-valve 54 via the flange 55 and the nozzle 53.

The four L-valves 34, 38, 52, and 54 are symmetrically spaced every 90 degrees around the circumference of the riser-reactor 40, as shown in FIG. 3. Generally, the number of L-valves is the same as the number of portions into which the stream in the line 18 is divided, and is also the same as the number of recirculation pipes or conduits passing from the bottom of the catalyst withdrawal zone 46, which is described hereinafter. For a given geometrical arrangement of an L-valve, the flow rate of the stream passing through each flange and nozzle regulates the flow rate of catalyst flowing downward through the L-valve. Thus, the flow rate of isobutane through each nozzle 27, 30, 51, and 53 regulates the flow rate of catalyst that flows through recirculation pipes 34V, 38V, 52V, and 54V, respectively. Means for regulating the flow rates of the four portions that are produced by dividing the stream that flows in line 18 are conventional and are not shown in the Figures or described herein.

In addition to its flange and nozzle, each L-valve consists of a valve inlet, which is referred to herein as a recirculation pipe, and a valve outlet, which is referred to herein as a feeder pipe. Each recirculation pipe is substantially vertical and each feeder pipe is substantially horizontal. The term "substantially horizontal" as used herein means generally less than 5°, and preferably less than 1°, from the horizontal. Thus, L-valve 34 includes the recirculation pipe 34V and a feeder pipe 34H, L-valve 38 includes the recirculation pipe 38V and a feeder pipe 38H, L-valve 52 includes the recirculation pipe 52V and a feeder pipe 52H, and L-valve 54 includes the recirculation pipe 54V and a feeder pipe 54H. The upper or inlet end of each recirculation pipe, 34V, 38V, 52V, or 54V, is connected to a bottom head 44 of vessel 10 and communicates with the catalyst withdrawal zone 46 therein. The outlet end of each feeder pipe is connected to the bottom 41 of riser-reactor 40 and communicates with the space 43 in the bottom of the riser-reactor 40.

Catalyst particles enter each L-valve from the bottom of the catalyst withdrawal zone 46, flow downwardly through that L-valve's recirculation pipe, pass around and by that L-valve's nozzle, and flow horizontally through that L-valve's feeder pipe to the bottom of the riser-reactor 40. The upper ends of the recirculation pipes 34V, 38V, 52V, and 54V, are symmetrically spaced 90 degrees apart around the bottom of an annular catalyst bed of the catalyst withdrawal zone 46. In addition, the feeder pipes 34H, 38H, 52H, and 54H, are symmetrically routed to the bottom 41 of riser-reactor 40. In this way, catalyst can be symmetrically or uniformly withdrawn from the entire circumference of catalyst withdrawal zone 46. Generally, there are at least two recirculation pipes through which catalyst is withdrawn from the catalyst withdrawal zone 46 to ensure that the catalyst can be withdrawn symmetrically or uniformly Provided that there are at least two recirculation pipes, the number of recirculation pipes is not an essential element of this invention, and 8, 10, 12, or more recirculation pipes may be used.

The catalyst particles in each recirculation pipe 34V, 38V, 52V, or 54V form a packed bed in each pipe. The packed bed in each recirculation pipe is statically supported by the catalyst that extends from the bottom of each recirculation pipe and into each corresponding feeder pipe, which in turn is statically supported by the corresponding feeder pipe wall. The catalyst particles that fill the intersection between each recirculation pipe and its corresponding feeder pipe (i.e. intersection 35 of pipes 34V and 34H and intersection 37 of pipes 38V and 38H) also form a packed bed as do the particles that fill the feeder pipe at least part-way along the length of the feeder pipe between the corresponding recirculation pipe and the bottom of the riser-reactor 40. The dimensions of each feeder pipe 34H, 38H, 52H, or 54H are such that catalyst does not flow through L-valve 34, 38, 52, or 54, respectively, unless isobutane is being introduced through nozzle 27, 30, 51, or 53, respectively.

Each nozzle 27, 30, 51, or 53 extends from each flange 28, 32, 49, or 55, respectively, through the wall of each recirculation pipe 34V, 38V, 52V, or 54V, respectively. The discharge end of each nozzle 27, 30, 51, or 53 is preferably flush with the inside surface of each recirculation pipe 34V, 38V, 52V, or 54V, respectively. Thus, the discharge end 29 of nozzle 27 is preferably flush with the inside surface of recirculation pipe 34V, and the discharge end 31 of nozzle 30 is preferably flush with the inside surface of recirculation pipe 38V. At the discharge end of each of the nozzles 27, 30, 51, or 53, the bottom of the inside bore of the nozzle is preferably higher than the top of the inside bore of each of the corresponding feeder pipe 34H, 38H, 52H, or 54H. The length of each feeder pipe 34H, 38H, 52H, or 54H is preferably from 6 to 10 times the diameter of the bore opening in each feeder pipe. This helps to ensure that once the flow of catalyst particles through each feeder pipe begins, the catalyst particles flow as a moving packed bed in essentially plug flow through the feeder pipe. This also helps minimize settling out of the catalyst particles in the feeder pipe.

The flow of catalyst particles through each feeder pipe radially inward toward the space 43 at the bottom portion 41 of riser-reactor 40 is started by initiating a flow of the isobutane-containing stream through the nozzle that corresponds to that feeder pipe's L-valve, the rate of flow being sufficient to overcome the resistance to catalyst flow through that feeder pipe. As the flow of the isobutane-containing stream through that nozzle increases, the flow rate of catalyst through the corresponding L-valve increases, and the flow rate through that nozzle can be increased until the catalyst flows freely toward the bottom portion 41 of riser-reactor 40. The flow rate of the isobutane-containing portion through each nozzle is controlled by valves (not shown). The total flow rate of catalyst through all of the feeder pipes, 34H, 38H, 52H, and 54H, toward the riser-reactor 40 can be increased up to the maximum rate at which the catalyst can flow upward from the bottom portion 41 of the riser-reactor 40. The flow rates of catalyst through each of the individual catalyst recirculation pipes are preferably the same, but it is not a requirement of this invention that catalyst flows through each recirculation pipe at the same rate. Accordingly, the catalyst rate through any one individual recirculation pipe is generally within 50%, preferably within 10%, and more preferably within 5% of the quotient of the total catalyst rate through all of the recirculation pipes divided by the number of recirculation pipes. If two feeder pipes are oriented from about 170 to about 190° opposite from one another (e.g. the pair of 34H and 38H, and the pair of 52H and 54H) in the same plane (e.g., the plane of the feeder pipes 34H, 38H, 52H, and 54H), then the difference between the catalyst flow rates through the two pipes is less than 5% of the average of the total catalyst rate through both feeder pipes. This helps to ensure uniform mixing and to minimize erosion at the bottom portion 41 of riser-reactor 40.

In general, most of the isobutane-containing stream that enters the nozzle 27, 30, 51, or 53 of L-valve 34, 38, 52, or 54, respectively, flows cocurrently with the catalyst particles through the feeder pipe 34H, 38H, 52H, or 54H, respectively. However, a portion of the entering isobutane-containing stream may flow countercurrently to the catalyst particles through the recirculation pipe 34V, 38V, 52V, or 54V, respectively. This countercurrent contacting with isobutane of the catalyst particles in the recirculation pipes helps to flush any residual hydrogen from the void volume and the pore volume of the catalyst particles. As described hereinafter, the origin of the hydrogen may be the liquid phase (e.g., mild) regeneration, vapor phase (e.g., severe) regeneration, or both regenerations, and the flushing prevents hydrogen from saturating the butene isomer feed. The flushing of the catalyst particles that takes place in the recirculation pipes may be instead of, or in addition to, any flushing that occurs prior to the entry of the catalyst particles into the recirculation pipes.

The space 43 along the central axis of riser-reactor 40 is the point where the isobutane and the catalyst that flow radially inward through feeder pipes 34H, 38H, 52H, and 54H combines with the mixture of isobutane and butene isomers that enters the bottom portion 41 of the riser-reactor 40 through the flange 26 and the nozzle 25. In combination with the inwardly-flowing fluid in the feeder pipes, the upwardly-flowing fluid through nozzle 25 is sufficient to fluidize the inwardly-flowing catalyst particles in the feeder pipes. The catalyst particles are fluidized in the space 43 or in the lower portion of riser-reactor 40 and remain in a fluidized state within a space 39 along the length of riser-reactor 40. The flow rate of the mixture entering through nozzle 25 is also sufficient, along with the isobutane flowing through the feeder pipes, to satisfy the requirements for the molar ratio of isobutane to olefin in the riser-reactor 40. Additional olefin (not shown) may be added to the riser-reactor 40 at multiple points along the length of riser-reactor 40. The amount of catalyst that is fluidized upward in riser-reactor 40 is sufficient to satisfy the requirements of the weight ratio of catalyst to olefin in the riser-reactor 40.

At the top 42 of riser-reactor 40, the effluent of the riser-reactor 40 discharges into a separation zone 60 within the vessel 10. The effluent of the riser-reactor 40 contains the product alkylate which comprises hydrocarbons having from 5 to 12 or more carbon atoms, any residual or unreacted isobutane, and catalyst particles. In the separation zone 60, the alkylate and the isobutane separate from the catalyst particles. The separation zone 60 may use any of a variety of liquid-solid separation devices, such as cyclones, baffles, screens, or a quiescent zone, for separating the liquid alkylate and liquid isobutane from the solid catalyst particles, and the particular device that is used is not an essential element of this invention. The alkylate and the isobutane pass through line 82 to conventional facilities, which are not shown, for recycling of the isobutane and recovery of the product alkylate.

The catalyst particles pass downward from the separation zone 60 and form a catalyst particle bed 64 having an upper limit or surface 62. Although the catalyst particles in bed 64 may be fluidized to any extent above the point of minimum fluidization, preferably the bed 64 is a dense fluidized bed or a moving packed bed. The catalyst particles in the bed 64 may be contacted with fluids, such as liquid isobutane saturated with hydrogen, in order to at least partially restore catalyst activity or catalyst selectivity that may have been lost as a result of the reactions that take place in the presence of the catalyst particles in the riser-reactor 40. The fluid may contact the catalyst in a cocurrent, countercurrent, or cross-current direction, or in a combination of directions.

Such contacting for the purpose of restoring activity or selectivity may require subdividing the bed 64 into two or more zones. For example, the bed 64 may be subdivided into three zones: an upper zone, a middle zone, and a lower zone. The upper zone, which is not separately denoted in the Figures, may be a liquid phase, or mild, regeneration zone, where the catalyst particles are contacted with hydrogen saturated isobutane liquid in order to desorb alkylate and heavy hydrocarbons from the catalyst particles. The term "heavy hydrocarbons" as used herein refers to hydrocarbons that are heavier than the desired alkylate product. Heavy hydrocarbons may have formed as by-products of side reactions in the riser-reactor 40. The middle zone, which is also not separately denoted in the Figures, may be a flushing zone, where the catalyst particles are contacted with isobutane in order to remove residual hydrogen from the void volume and the pore volume of the catalyst particles. The lower zone, which is denoted as 46, is the previously-mentioned and hereinafter-described catalyst withdrawal zone, from which the L-valves 34, 38, 52, and 54 withdraw and recirculate catalyst particles to the bottom 41 of the riser-reactor 40.

Where bed 64 is subdivided into two or more zones, conventional fluid flow and particle distributors may be used to divide or separate the zones from each other. Such conventional distributors include pipe distributors, conical baffles, and annular baffles. Annular baffles are disclosed in U.S. Pat. No. 4,662,081 (Greenwood), U.S. Pat. No. 4,665,632 (Greenwood), and U.S. Pat. No. 5,397,458 (Micklich et al.).

In the catalyst withdrawal zone 46, the catalyst particles preferably form a moving packed bed, but a moving packed bed in the catalyst withdrawal zone 46 is not an essential element of this invention. If the catalyst particles form a moving packed bed in the catalyst withdrawal zone 46, the catalyst withdrawal zone 46 is preferably defined in part by a frustro-conical section 44, which helps insure uniform or plug flow of solid particles being withdrawn from a moving packed bed. Frustro-conical sections are well-known to persons of ordinary skill in the art of solids flow and mass flow hoppers. The catalyst withdrawal zone 46 is also in part defined by an inverted frustro-conical section 48 that help,s to ensure plug flow of catalyst particles in a moving packed bed that descend along or near the surface of the riser-reactor 40.

Most of the catalyst particles that leave the catalyst withdrawal zone 46 exit, as described previously, via the recirculation pipes 34H, 38H, 52H, and 54H. As described previously, the number of recirculation pipes is not an essential element of this invention, provided there are at least two recirculation pipes. A second and relatively small portion of the catalyst particles flowing through the catalyst withdrawal zone 46 exits through a line 42. The catalyst particles in the line 42 passes to the junction of lines 68 and 70, where it combines with recycle isobutane from a line 74 and makeup isobutane from a line 66. The combined flow of recycle and makeup isobutane flows through the line 68 and educts the catalyst from the line 42 upward through the line 70, thereby controlling the withdrawal rate of catalyst through the line 42 from the catalyst withdrawal zone 46. Line 42 preferably extends diagonally downward from vessel 10 to the junction of lines 68 and 70, and line 70 preferably extends vertically to an elevation above the top of a severe regeneration zone 80. At that elevation, line 70 bends and extends horizontally to a point directly above the severe regeneration zone 80, and from that point line 70 bends and extends vertically downward to severe regeneration zone 80.

The severe regeneration zone 80 can be any of a number of regeneration designs, and it is not critical to the success of this invention that any one particular severe regeneration zone be used. The purpose of the severe regeneration zone is to remove from the catalyst surface adsorbed heavy hydrocarbons that typically are not removed in the liquid phase, or mild, regeneration step. The severe regeneration zone can operate in liquid or vapor phase. Liquid phase severe regeneration can comprise contacting the catalyst with hydrogen-saturated isobutane at a temperature that is higher than that of the liquid phase regeneration step, whereas vapor phase severe regeneration can comprise contacting the catalyst with a hot hydrogen-rich stream. Although a number of different severe regeneration zones are suitable for use with this invention, different severe regeneration zones have different features and characteristics, such as the extent to which the adsorbed heavy hydrocarbons are removed from a particular catalyst, and the type and cost of necessary equipment, such as vessels, pumps, and heat exchangers. In particular, vapor phase severe regeneration may employ a drying zone to remove isobutane from the catalyst prior to the catalyst's entering the severe regeneration zone and a rewetting zone to contact the severely regenerated catalyst with liquid isobutane prior to the catalyst's entering the liquid phase regeneration zone.

The heavy hydrocarbons that are desorbed from the catalyst by severe regeneration are withdrawn from the severe regeneration zone 80 in a vent stream that flows through a line 72. The vent stream contains those heavy hydrocarbons, but the balance of the vent stream depends on the particular method of severe regeneration that is employed. For example, in addition to the heavy hydrocarbons, the vent stream may contain whatever medium is employed for severe regeneration, such as liquid isobutane or a vapor. The method for recovering the desorbed heavy hydrocarbons from the vent stream depends on the vent stream's composition, temperature and pressure. Persons of ordinary skill in the art of hydrocarbon processing are able to design, build, and operate processes either for disposing of the vent stream or for separating the heavy hydrocarbons from the vent stream in order to recover and recycle the severe regeneration medium to the severe regeneration zone 80. Some of the isobutane that was employed to lift the catalyst particles through line 70 is recycled from the severe regeneration zone 80 through line 74 to lift more catalyst particles.

Catalyst particles flow by gravity from the severe regeneration zone 80 to vessel 10 without the need for a lift. Line 76 extends into vessel 10 so that the bottom 84 of line 76 discharges the severely regenerated catalyst particles into vessel 10. The bottom 84 of line 76 can discharge the catalyst particles into any zone or zones of the catalyst bed 64, into the L-valves 34, 38, 52, and 54, or directly into the space 43 at the bottom 41 of the riser-reactor 40. If the line 76 discharges into the space 43, then the four feeder pipes, 34H, 38H, 52H, and 54H, and the line 76 could all be symmetrically spaced 72° apart around the bottom 41 of the riser-reactor 40. But, in such a case, in order to ensure uniform and symmetric introduction of catalyst into the space 43, it is preferred to maintain the symmetric 90° spacing of the four feeder pipes as shown in the Figures and to route line 76 into the space 43, but above the plane of the feeder pipes 34H, 38H, 52H, and 54H.

Figure 4:
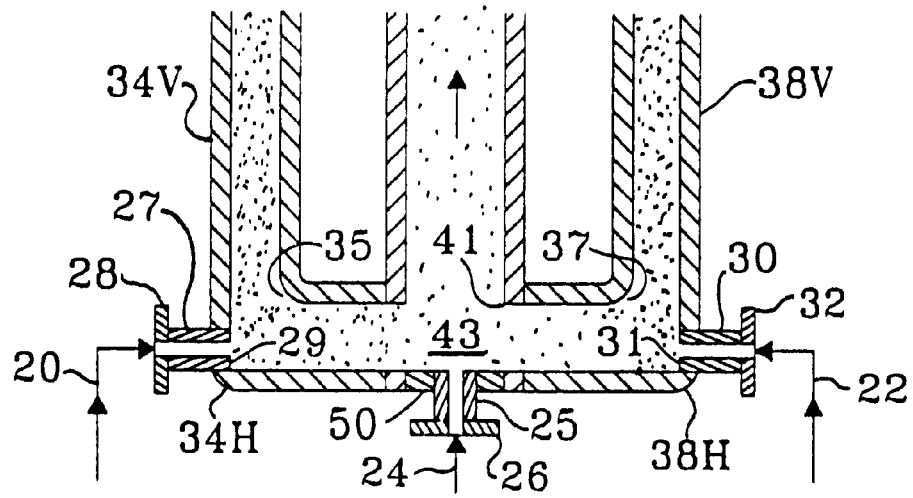
FIGS. 4 and 5 show alternatives to the details shown in FIG. 2.
Figure 5:
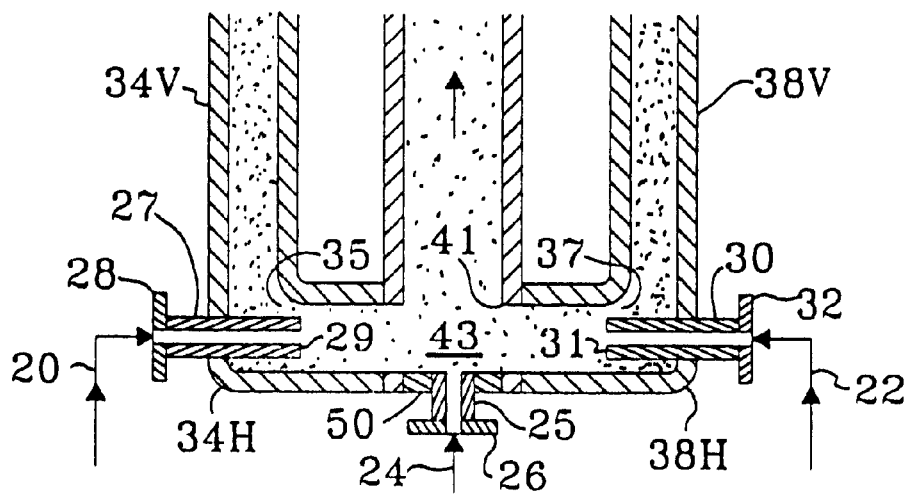

FIGS. 4 and 5 show alternative arrangements for the nozzle that introduces the isobutane-containing stream into each L-valve. Items in FIGS. 4 and 5 that correspond to items in FIG. 2 have been given the same item number. In FIG. 4, the discharge end of each nozzle is flush with the inside surface of each recirculation pipe, and at the discharge end not only the bottom but also the top of the inside bore of each nozzle is below the top of the inside bore of the corresponding feeder pipe. Alternatively, although not shown in FIG. 4, the bottom of the inside bore of each nozzle could be at the same elevation as, or flush with, the bottom of the inside bore of the corresponding feeder pipe. In FIG. 5, the discharge end of each nozzle extends beyond the inside surface of each recirculation pipe, past the intersection of the recirculation pipe and its corresponding feeder pipe, and into the feeder pipe.

The subject process can be performed using any solid, that is, heterogeneous, catalyst which is stable and has the required activity and selectivity for the desired reaction at the conditions needed to maintain liquid phase reactants in the riser-reactor. A large number of catalysts have been proposed for the production of motor fuel by alkylation including various zeolites and superacid catalysts. Suitable superacid catalysts include sulfated zirconia and tungstated zirconia. U.S. Pat. No. 4,384,161 describes the use of a large pore zeolite and a Lewis acid. The zeolites referred to include ZSM-4, ZSM-3, the faujasites including zeolite Y and mordenite. The Lewis acids mentioned in this reference include boron trifluoride and aluminum chloride. The alkylation of isoparaffins using a somewhat similar catalyst system comprising a large pore crystalline molecular sieve such as a pillared silicate or an aluminophosphate or silicoaluminophosphate together with a gaseous Lewis acid is disclosed in U.S. Pat. No. 4,935,577. The use of these Lewis acids is not preferred in the subject process as they provide their own waste handling and safety problems. They also will probably require provisions for the circulation of the Lewis acid, which may complicate the process as shown by the teaching of the just cited U.S. Pat. No. 4,935,577. U.S. Pat. No. 5,157,200 describes an isoparaffin alkylation process using a catalyst comprising a crystalline transition alumina, preferably eta or gamma alumina, which has been treated with a Lewis acid under anhydrous conditions. Previously referred to U.S. Pat. No. 5,157,196 describes an isoparaffin alkylation process using a slurried solid catalyst, with the preferred catalyst being an acid washed silica which has been treated with antimony pentafluoride. Both of these last two references describe a number of prior art solid bed paraffin alkylation catalysts.

A preferred paraffin alkylation catalyst comprises a refractory inorganic oxide impregnated with a monovalent cation, especially an alkali metal cation or an alkaline earth metal cation, and whose bound surface hydroxyl groups have been at least partially reacted with a Friedel-Crafts metal halide. Analogs of these catalysts without the metal cations are described in U.S. Pat. Nos. 2,999,074 and 3,318,820 which describe preparation techniques which can be applied to the preferred catalysts. The preferred refractory oxide is alumina having a surface area greater than 50 $m^2/g$, but the use of other oxides including titania, zirconia, silica, boria and aluminum phosphate is contemplated. The preferred catalyst also contains a metal component active for olefin hydrogenation deposited on the inorganic oxide prior to reaction of the bound surface hydroxyl groups with the metal halides. This metal may be chosen from the group consisting of nickel, platinum, palladium, and ruthenium with the first three of these metals being preferred. The catalyst contains one or more monovalent metal or alkaline earth metal cations selected from the group consisting of lithium, sodium, potassium, cesium, silver, copper, beryllium, magnesium, calcium and barium. Subsequent to the deposition of these metals and the controlled calcination of the composite, the composite is reacted with a Friedel-Crafts metal halide. The metal may be aluminum, zirconium, tin, tantalum, gallium, antimony or boron. Suitable halides are the fluorides, chlorides and bromides.

The presence of a highly active metal hydrogenation component on the catalyst will promote hydrogenation of the substrate olefin if both the olefin and hydrogen simultaneously contact the catalyst. This potential waste of the olefin and hydrogen can be avoided by careful design and operation of the process to avoid having both the olefin and hydrogen in simultaneous contact with the catalyst. This can be done by flushing the hydrogen or olefin from the catalyst before inserting it into a zone containing the other compound as described above.

Silicalites have been described as useful alkylation catalysts for the production of monoalkylbenzenes in U.S. Pat. No. 4,489,214 (J. R. Butler et al.) and as useful in methylating toluene to produce paraxylene in U.S. Pat. No. 4,444,989 (F. E. Herkes.) The use of ZSM-5 zeolites in aromatic alkylation is described in U.S. Pat. No. 3,751,506. ZSM-5 zeolites that have been treated with one or more compounds or elements to improve their selectivity for paraselective alkylation of aromatic hydrocarbons are described in U.S. Pat. No. 4,420,418. The use of zeolite L, zeolite Omega, and zeolite beta as alkylation catalysts for the selective alkylation of benzene is described in U.S. Pat. No. 4,301,316. The use of a number of natural and synthetic zeolites including clinoptilolite and zeolite Y as alkylation catalysts is described in U.S. Pat. No. 3,251,897.

The catalyst may be in the form of any suitable shape and size which results in a solid catalyst which flows readily in both dry and wet states and which is readily fluidized at the moderate liquid flow rates employed in the riser-reactor. The catalyst can therefore be present as small irregular particles or as uniformly shaped particles. It is preferred that the catalyst is present as "microspheres" that are substantially spherical and that have an average diameter of from about 0.1 to about 2.0 mm and more preferably less than about 1.0 mm.

The catalyst is generally employed in a transport reactor such as a riser-reactor. Although the direction of flow of hydrocarbons and catalyst through the transport reactor is preferably upward, the direction may also be downward, horizontal, a combination of directions, or a direction that is intermediate between those directions. Suitable operating conditions for the riser-reactor include a temperature of from about −50 to about 100° C. (−58 to 212° F.), preferably from about 10 to about 40° C. (50 to 104° F.), and a pressure as required to maintain the hydrocarbons present as a liquid. A moderate pressure in the general range of from about 1380 to about 4830 kpa(g) (200 to 700 psi(g)) is preferred with from about 3100 to about 4140 kpa(g) (450 to 600 psi(g)) being highly preferred. The weight ratio of catalyst per olefin in the riser-reactor is generally from about 3 to about 10. The liquid residence time in the riser-reactor is in the general range of from about 60 to about 150 seconds, and the catalyst residence time is in the general range of from about 90 to about 300 seconds. The riser-reactor is preferably designed and operated in a manner intended to promote plug flow (minimal backmixing) of the reactants, products and catalyst within the riser-reactor. However, the liquid must flow upward faster than the catalyst in order to transport it.

It is generally preferred that the riser-reactor is operated with an excess of the substrate hydrocarbon compared to the alkylating agent. That is, it is preferred to operate with a ratio of the substrate paraffinic or aromatic hydrocarbon to an alkylating agent olefin at the reactor or tube entrance greater than 1:1, and preferably from about 5:1 to about 20:1 or higher as measured by the flow rates into the riser-reactor. It is highly preferred to operate with an abundance of isoparaffin compared to alkylating agent in a motor fuel alkylation process. Specifically, it is preferred that the molar ratio of isoparaffin to olefin being charged to the riser-reactor is greater than 2:1 and more preferably greater than 8:1. Ratios of 10:1 or higher can be employed for motor fuel alkylation, but ratios of about 100:1 or higher are generally considered to be uneconomical. Injection of the olefin at a number of points along the flow path of the hydrocarbon through the riser-reactor may be employed to maintain a higher average paraffin to olefin ratio, and preferably three injection points, in addition to the olefin injection at the bottom of the riser-reactor, are used. So, there are generally four or more olefin injection points along the length of the riser-reactor.

Provisions may be made for removing used catalyst from the process and to replace the used catalyst with fresh catalyst. Conventional-valved lock hopper systems may be used for this purpose.

What is claimed is:

1. A process for the alkylation of an alkylation substrate with an alkylating agent, the process comprising the steps of:

a) passing to an alkylation transport reactor an alkylating agent, a feed stream comprising an alkylation substrate, and a plurality of recirculation stream comprising catalyst particles and the alkylation substrate, wherein the plurality of recirculation streams flows in a plurality of substantially horizontal directions substantially disposed in a plane and wherein die plurality of recirculation streams passes symmetrically to the alkylation transport reactor;

b) alkylating the alkylation substrate with the alkylating agent in the presence of a fluidized bed of catalyst particles at alkylation conditions in the alkylation transport reactor, and producing alkylate;

c) passing a transport reactor effluent stream comprising alkylate and catalyst particles from the alkylation transport reactor to a separation zone, separating the transport reactor effluent stream in the separation zone, and recovering from the separation zone a first annular moving packed bed comprising catalyst particles and a product stream comprising alkylate, wherein the first annular moving packed bed has a first inner diameter;

d) passing catalyst particles from the first annular moving packed bed to a second annular moving packed bed, wherein the second annular moving packed bed has a second inner diameter that is greater than the first inner diameter;

e) passing a plurality of portions of the catalyst particles at a plurality of particle flow rates from the second annular moving packed bed to a plurality of fluid-controlled valves, wherein the plurality of particle flow rates are within 50% of the average of the plurality of particle flow rates;

f) passing the alkylation substrate to the plurality of fluid-controlled valves to produce the plurality of recirculation streams and to deliver catalyst particles to the alkylation transport reactor; and g) passing an additional portion of the catalyst particles from the second annular moving packed bed to a catalyst regeneration zone, at least partially reactivating catalyst particles in the catalyst regeneration zone, and passing a supplemental portion of catalyst particles from the catalyst regeneration zone to the alkylation transport reactor, wherein the introduction of the supplemental portion to the alkylation transport reactor is above the plane.

2. The process of claim 1 further characterized in that the alkylation conditions comprise at least a partial liquid phase.

3. The process of claim 1 further characterized in that the alkylation substrate is a paraffinic hydrocarbon having from 4 to 6 carbon atoms.

4. The process of claim 3 wherein the paraffinic hydrocarbon is isobutane.

5. The process of claim 1 further characterized in that the alkylation agent is an olefinic hydrocarbon having from 2 to 6 carbon atoms.

6. The process of claim 5 wherein the olefinic hydrocarbon is a butene.

7. The process of claim 1 further characterized in that the catalyst particles are substantially spherical and have a diameter of from about 0.1 to about 2.0 mm.

8. The process of claim 1 further characterized in that Step (e) comprises passing the plurality of portions of the catalyst particles to a plurality of recirculation catalyst beds comprising a plurality of moving packed beds of catalyst particles and passing catalyst particles from the plurality of recirculation catalyst beds to the plurality of fluid-controlled valves.

9. The process of claim 8 further characterized in that a plurality of portions of the alkylation substrate that is passed to the plurality of fluid-controlled valves passes through the plurality of recirculation beds countercurrently to the flow of catalyst particles and enters the separation zone.

10. The process of claim 1 further characterized in that catalyst particles in the transport reactor effluent stream are at least partially deactivated, and the separation zone operates at at least partially at regeneration conditions sufficient to at least partially regenerate at least partially deactivated catalyst particles.

11. The process of claim 1 further characterized in that the alkylation transport reactor has a bottom portion and a top portion oriented above the bottom portion and at least one intermediate portion located between the bottom portion and the top portion and the alkylating agent is passed to the bottom portion and to the at least one intermediate portion of the alkylation transport reactor.

12. The process of claim 1 further characterized in that the alkylation transport reactor has a bottom portion and a top portion oriented above the bottom portion and three intermediate portions located between the bottom portion and the top portion and the alkylating agent is passed to the bottom portion and to the three intermediate portions of the alkylation transport reactor.

13. The process of claim 1 further characterized in that Step (f) comprises passing catalyst particles as a plurality of moving packed beds in essentially plug flow from the plurality of fluid-controlled valves to the alkylation transport reactor.

14. The process of claim 1 further characterized in that the plurality of portions of the catalyst particles passes substantially vertically downward.

15. The process of claim 1 wherein the plurality of particle flow rates are within 10% of the average of the plurality of particle flow rates.

16. A process for the alkylation of isobutane with butenes, the process comprising the steps of:

a) passing into a substantially vertical alkylation riser-reactor a feed stream comprising isobutane and a plurality of recirculation streams comprising catalyst particles and isobutane, wherein the riser-reactor has a bottom portion and a top portion oriented above the bottom portion, and wherein the feed stream and the plurality of recirculation streams enter the bottom portion of the riser-reactor, the plurality of recirculation streams flows in a substantially horizontal direction, wherein the directions of the flows of the plurality of recirculation streams are disposed in a plane;

b) passing butenes to the bottom portion of the riser-reactor and to at least three intermediate portions of the riser-reactor, wherein the at least three intermediate portions are located between the bottom portion and the top portion of the riser-reactor;

c) alkylating isobutane with butenes in the presence of a fluidized bed of catalyst particles at alkylation conditions in the riser-reactor, and producing alkylate;

d) discharging a riser-reactor effluent stream comprising alkylate and catalyst particles that are partially deactivated from the top portion of the riser-reactor to a separation zone, separating the riser-reactor effluent stream in the separation zone into a product stream comprising alkylate that is recovered from the process and into catalyst particles that are partially deactivated and that pass downwardly in the separation zone;

e) forming a first annular moving packed bed of catalyst particles that are partially deactivated in a lower portion of the separation zone, the first annular moving packed bed having a first inner diameter;

f) contacting the catalyst particles in the first annular moving packed bed in the lower portion of the separation zone with isobutane and hydrogen at reactivation conditions sufficient to at least partially reactivate the catalyst particles in the first annular moving packed bed;

g) passing catalyst particles from the first annular moving packed bed to a second annular moving packed bed, wherein the second annular moving packed bed has a second inner diameter that is greater than the first inner diameter;

h) passing a plurality of aliquot portions of catalyst particles from the second annular moving packed bed to a plurality of substantially vertical recirculation conduits, and forming in the plurality of recirculation conduits a plurality of moving packed beds of catalyst particles;

i) passing catalyst particles downwardly at a plurality of particle flow rates through the plurality of moving packed beds to a plurality of fluid-controlled valves, wherein the plurality of particle flow rates are within 50% of the average of the plurality of particle flow rates;

j) passing isobutane to the plurality of fluid-controlled valves to produce the plurality of recirculation streams and to deliver catalyst particles to a plurality of substantially horizontal feeder conduits;

k) conveying the plurality of recirculation streams through the plurality of feeder conduits and to the bottom portion of the riser-reactor; and l) passing an additional portion of the catalyst particles from the second annular moving packed bed to a catalyst regeneration zone, at least partially reactivating catalyst particles in the catalyst regeneration zone, and passing a supplemental portion of catalyst particles from the catalyst regeneration zone to the alkylation transport reactor, wherein the introduction of the supplemental portion to the alkylation transport reactor is above the plane.

* * * * *

UNITED STATES PATENT AND TRADEMARK OFFICE
CERTIFICATE OF CORRECTION

PATENT NO. : 6,486,374 B1
DATED : November 26, 2002
INVENTOR(S) : William H. Radcliffe et al.

It is certified that error appears in the above-identified patent and that said Letters Patent is hereby corrected as shown below:

Column 14,
Line 54, "stream" should be replaced with the word "streams"

Column 15,
Line 61, the word "at" was mistakenly repeated immediately following the first occurrence of "at" on line 61 so one occurrence of the word "at" should be deleted.

Signed and Sealed this

First Day of April, 2003

JAMES E. ROGAN
*Director of the United States Patent and Trademark Office*